United States Patent [19]
Kim et al.

[11] Patent Number: 5,386,030
[45] Date of Patent: Jan. 31, 1995

[54] ANTIVIRAL (PHOSPHONOMETHOXY)METHOXY PURINE/PYRIMIDINE DERIVATIVES

[75] Inventors: Choung U. Kim, Madison; John C. Martin, Cheshire; Bing Y. Luh, Killingworth; Peter F. Misco, Durham, all of Conn.

[73] Assignees: Institute of Organic Chemistry and Biochemistry of the Academy of Science of the Czech Republic, Czech Rep.; Rega Stichting v.z.w., Belgium

[21] Appl. No.: 16,401

[22] Filed: Feb. 11, 1993

Related U.S. Application Data

[62] Division of Ser. No. 619,856, Nov. 29, 1990, Pat. No. 5,208,221.

[51] Int. Cl.$^6$ .............................. C07F 9/02
[52] U.S. Cl. .................... 544/243; 544/244; 558/87; 558/177; 558/189
[58] Field of Search ............... 558/87, 177, 189; 544/243, 244

[56] References Cited

U.S. PATENT DOCUMENTS
5,108,994 4/1992 Harnden et al. .................. 514/81

FOREIGN PATENT DOCUMENTS
0404296A1 12/1990 European Pat. Off. ..
494370 7/1992 European Pat. Off. ..

OTHER PUBLICATIONS
Nurtdinov et al. Chem Abst 92(9):76614y (1979).
Shergina et al., Chem Abst. 98(13):83664d (1972).
Pudovik et al., Chem Abst 69(7):27492y (1968).
Kim et al., Tetrahedron Lett. 33(1) 25-8 (1992).
Nurtdinov et al., Chem. Abst 111(15):134335g (1989).
Nurtdinov et al., Chem. Abst. 96(7):52396k (1980).
Vyshinskaya et al., Chem. Abst. 92(11):94511s (1978).

*Primary Examiner*—Cecilia Tsang
*Attorney, Agent, or Firm*—Daryl D. Muenchau

[57] ABSTRACT

The present invention concerns nucleotide analogs and their compositions and use. In particular it relates to novel (phosphonomethoxy) methoxy purine/pyrimidine derivatives.

13 Claims, No Drawings

ANTIVIRAL (PHOSPHONOMETHOXY)METHOXY PURINE/PYRIMIDINE DERIVATIVES

This application is a division of application Ser. No. 07/619,856 filed on Nov. 29, 1990, now U.S. Pat. No. 5,208,221.

BACKGROUND OF THE INVENTION

1. Field of the Invention

The present invention concerns nucleotide analogs and their compositions and use. In particular it relates to novel (phosphonomethoxy) methoxy purine/pyrimidine derivatives.

2. Background of the Invention

Infectious viral diseases are recognized as an important medical problem. Progress against infectious viral disease requires the development of drugs with antiviral activity while remaining benign to normal cell lines. Among the antiviral agents currently under study which seem to possess selectivity are nucleoside analogs. In general, these compounds are structural analogs of the naturally occurring nucleosides. Structural modification in either the purine or pyrimidine base nucleus and/or the saccharide component results in a synthetically modified nucleoside derivative which, when incorporated into a viral nucleic acid forming process, acts to disrupt further synthesis of viral nucleic acid.

Effectiveness of these antiviral agents depends on selective conversion by viral enzymes, but not by host enzymes, to the corresponding nucleotide analog which is then converted to the triphosphate and incorporation into viral nucleic acid occurs. A problem with this antiviral strategy has been the emergence of certain viral strains whose enzymes poorly promote phosphorylation of the nucleoside analogs. To circumvent this problem, intact nucleotide analogs appear to be potentially quite useful as antivirals for incorporation into viral nucleic acid.

A number of 3-hydroxy-2-phosphonylmethoxypropyl (HPMP) and 2-phosphonylmethoxyethyl (PME) derivatives of purine and pyrimidine have been evaluated for their antiviral properties. Gangemi, et al., *Antimicrobial Agents and Chemotherapy*, Vol. 33, No. 11, pp 1864–1868 (1989). The compounds of the present invention are isosteres of PME and HPMP purine and pyrimidine analogs.

European Patent Application EP-319,228 of Harnden, published Jun. 7, 1989, discloses a purine derivatives carrying a 9-phosphonomethoxyalkyloxy substituent (Formula I) exhibiting antiviral activity

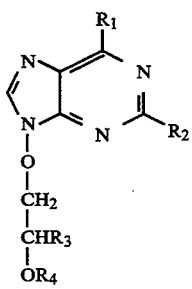

Formula I wherein $R_1$ is hydroxy, amino, chloro or $OR_7$; $R_7$ is $C_{1-6}$ alkyl, phenyl or phenyl $C_{1-2}$ alkyl either of which phenyl moieties may be substituted by one or two substituents selected from halo, $C_{1-4}$ alkyl or $C_{1-4}$ alkoxy; $R_2$ is amino or, when $R_1$ is hydroxy or amino, $R_2$ may also be hydrogen; $R_3$ is hydrogen, hydroxymethyl or acyloxymethyl; $R_4$ is a group of formula $CH_2P(O)(OR_5)(OR_6)$ wherein $R_5$ and $R_6$ are independently selected from hydrogen $C_{1-6}$ alkyl and optionally phenyl; or $R_3$ and $R_4$ together are $CH_2P(O)(OR_6)(OCH_2)$ wherein $R_6$ is as previously described. The compound of the present invention differ from the compounds of EP-319,228 by the presence of the acetal group in the compounds of the present invention.

Reist and Strum in PCT/US 84/00737, published Dec. 6, 1984, disclosed new phosphonic acid analogs of nucleoside phosphates which are useful as antivirals for incorporation into viral DNA. The structural formula for these compounds is shown below as Formula II.

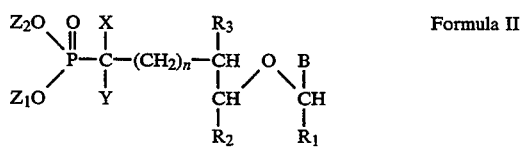

Formula II wherein B is a purine or pyrimidine base; $R^1$ and $R^2$ together complete a beta-pentofuranose sugar or $R^1$ is H and $R^2$ is H or hydroxymethyl; $R^3$ is H or OH; X is H, OH or together with Y is carbonyl oxygen and Y can also be H; $Z^1$ and $Z^2$ are H or alkyl.

Similarly, synthesis and anti-herpesvirus activity of phosphate and phosphonate derivatives of 9-[(1,3-dihydroxy-2-propoxy)methyl]guanine (Formula III) was disclosed by Prisbe, et al., in *J. Med. Chem.*, 29: 671 (1986).

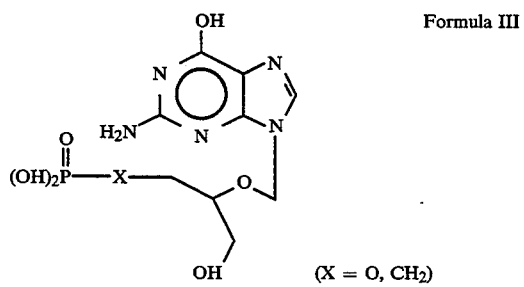

Formula III

Other phosphonate nucleotide analogs of the Formula III type wherein $X=CH_2$ have been described by R. M. Riggs et al, *Nucleosides and Nucleotides*, 8(5&6, 1119–1120 (1989); D. H. R. Bouton, et al., *Tetrahedron Letters*, No. 37, 30: 4969–4972 1972; and H. Tanaka, et al., *Tetrahedron Letters*, 30: 2567–2570 (1989).

Adenine phosphonic analogs (Formula IV) and their synthesis are disclosed in the UK Patent Application of Holy, et al., GB 2,134,907A published Aug. 22, 1984

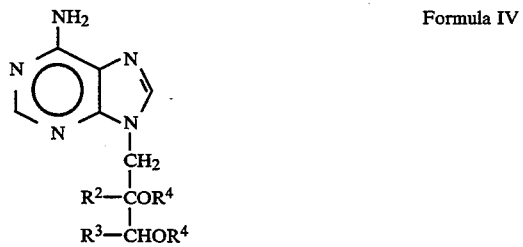

Formula IV wherein $R^2$ and $R^3$ are H or together complete a ribonucleoside ring; and both $R^4$ are alternately a hydrogen and $-CH_2P(O)(OH)_2$ group.

A preferred example of one of these compounds, known as (S)-HPMPA (Formula V) was disclosed by DeClercq, et al., in Nature, 323: 464–467 (1986) and earlier by Holy, et al, Nucleic Acids Research, Symposium Series No. 14, pp. 277–278 (1984). Phosphonate compounds which are HPMPA analogs are described in South African Patent 1987/8607. In applicant's hands, (S)-HPMPA is only slightly active in mice inoculated with herpes simples virus-2. In a 21 day protocol 30% of a group of animals treated i.p. with 50 mg/kg/day of (S)-HPMPA survived.

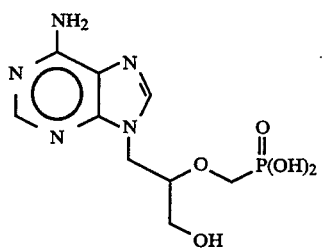

Formula V

European Patent Application EP-253,412 of A. Holy, et al, published on Jan. 20, 1988, discloses a series of N-phosphonylmethoxyalkyl derivatives of pyrimidine and purine bases (Formula VI) exhibiting antiviral activity

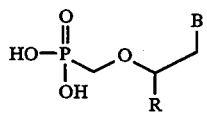

Formula VI in which R is a hydrogen atom or a hydroxymethyl group and B is an optinally substituted pyrimidin-1-yl, pyrimidin-3-yl, purin-3-yl, purin-7-yl, or purin-9-yl residue, whereby unsubstituted adenin-9-yl is excluded. Substituent B is preferably, inter alia, guanin-9-yl.

The addition of oxygen, while antiviral activity is retained, distinguishes the compounds of the present invention from the art. There is no teaching contained in these references, or a suggested combination thereof, which would suggest or make obvious the compounds, compositions, and uses involved in the present invention.

SUMMARY OF THE INVENTION

The present invention provides novel compounds having the Formula VII

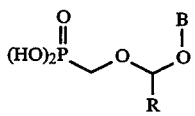

Formula VII wherein R and B are as defined below.

The present invention also provides a process for making the compounds of Formula VII.

The present invention further relates to useful intermediates and processes for their preparation.

The present invention further relates to a method of treating a warm blooded animal infected with a virus or a retrovirus with an effective amount of the compound of Formula VII.

The present invention further relates to a pharmaceutical composition for treating a warm blooded animal infected with a virus or a retrovirus which comprises an effective amount of the compound of Formula VII in association with a pharmaceutically acceptable substantially nontoxic carrier or excipient.

DETAILED DESCRIPTION OF THE INVENTION

The present invention provides novel purine/pyrimidine derivatives carrying (phosphonomethoxy)methoxy substitutions which compounds exhibit antiviral activity against herpes viruses and retroviruses, and which have the formula VII

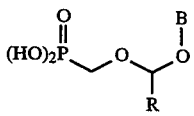

Formula VII wherein

R is hydrogen, alkyl having 1 to 6 carbon atoms, hydroxyalkyl with 1 to 6 carbon atoms, or haloalkyl having 1 to 6 carbon atoms; and B is a 9-substituted purine or 1-substituted pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine, cytosine, substituted cytosine, for example 5-ethylcytosine and 5-methylcytosine, thymine, uracil, 5-substituted uracil, for example 5-chlorouracil, 5-bromouracil, 5-ethyluracil, 5-iodouracil, 5-propyluracil and 5-vinyluracil, adenine and substituted adenine, for example, 3-deazaadenine, and pharmaceutically acceptable salts thereof, preferably adenine, substituted adenine, guanine, substituted guanine and pharmaceutically acceptable salts thereof.

The compounds of the present invention can exist as optical isomers and both racemic and diasteromeric mixtures of these isomers which may exist for certain compounds, as well as the individual optical isomers are all within the scope of the present invention. While the racemic mixtures can be separated into their individual isomers through well-known techniques such as, for example, the separation of diastereomeric salts formed with optically active adjuncts, e.g., acids or bases followed by conversion back to the optically active substrates; in most instances, for the compounds of the present invention, the preferred optical isomer can be synthesized by means of stereospecific reactions, beginning with the appropriate stereoisomer of the desired starting material.

As indicated above, the present invention also pertains to pharmaceutically acceptable non-toxic salts of these compounds, containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with the acid anion moiety of the phosphonic acid group. Metal salts can be prepared by reacting the metal hydroxide with a compounds of this invention. Examples of metal salts which can be prepared in this way are salts containing Li+, Na+, and K+. A less soluble metal salt can be precipitated form the solution of a more soluble salt by addition of the suitable metal compound. In addition, salts may be formed from acid addition of certain organic and inorganic acids, e.g., HCl, HBr, $H_2SO_4$ or organic sulfonic acids, with basic centers of the purine, specifically guanine, or pyrimidine base. Finally, it is to be understood that compounds of the present invention in their un-ionized, as well as zwitterionic form, and/or in the form, of solvates are also considered part of the present invention.

Compounds of the present invention also exist in subclasses, with two broad subclasses being those wherein B is either a purine or a pyrimidine base. Of these broad subclasses there are preferred classes wherein the purine base is a guanine or a substituted guanine moiety and where the pyrimidine bases are either thymine or cytosine. The most preferred class of compounds are those wherein B is guanine or substituted guanine.

The compounds of this invention, including the physiologically acceptable salts thereof, have desirable antiviral activity. They exhibit activity against viruses, for example, herpes simplex virus I, herpes simplex virus II, human cytomegalovirus, varicella zoster virus, influenza virus, vaccinia polio, rubella, small pox, cowpox, Epstein-Barr virus, measles virus, human respiratory virus, papillomavirus and sinbis virus. The compounds of this invention also exhibit activity against retroviruses, for example, murine leukemia virus (MuLV).

As mentioned above, the compounds of the present invention are useful active ingredients in human and veterinary medicine for the treatment and prophylaxis of diseases caused by retroviruses. Examples of fields of indication in human medicine regarding retroviruses are as follows:

(1) the treatment or prophylaxis of human retrovirus infections;
(2) the treatment or prophylaxis of diseases caused by HIV and the stages associated therewith such as Aids Related Complex (ARC) and lymph adenopathy syndrome (LAS) and the immune weakness and encephalopathy caused by this retrovirus;
(3) the treatment or prophylaxis of HTLV I infection or HTLV II infection;
(4) the treatment or prophylaxis of the AIDS carrier states (AIDS transmitter state); and
(5) the treatment or prophylaxis of diseases caused by hepatitis B virus.

Examples of indications in veterinary medicine are as follows:

(1) maedivisna (in sheep and goats);
(2) progressive pneumonia virus (PPV) (in sheep and goats);
(3) caprine arthritis encephalitis virus (in sheep and goats);
(4) zwoegerziekte virus (in sheep);
(5) infectious virus of anemia (of the horse); and
(6) infections caused by cat leukemia virus.

The compounds of Formula VII may be prepared by adding paraformaldehyde to diethylphosphonomethanol (1) in the presence of hydrochloric acid to give diethyl (Chloromethoxy)methylphosphonate (2). Displacement of compound 2 with $N_1$—O pyrimidine or $N_9$—O purine analogs gives the 9-[(diethylphosphono)-methoxy]methoxy purine or pyrimidine analog (3'). The 9-(phosphonomethoxy)methoxy purine or pyrimidine analog (4') is obtained by deblocking of the protecting group in compound 3'. See Reaction Scheme 1.

Reaction Scheme 1

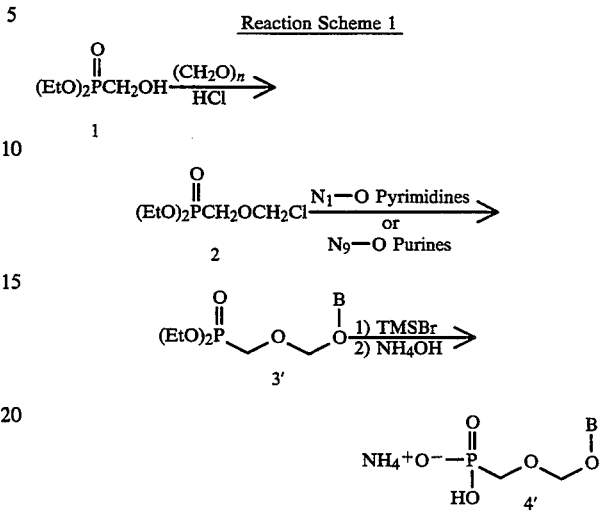

B = Pyrimidines
    Purines

In an alternate reaction route, the preparation of compounds of Formula VII may be prepared from intermediates of Formulas VIII, IX and X.

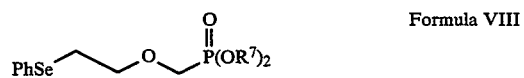

Formula VIII wherein R is alkyl $C_{1-4}$, or aryl;

Formula IX wherein R is alkyl $C_{1-4}$, or aryl; and

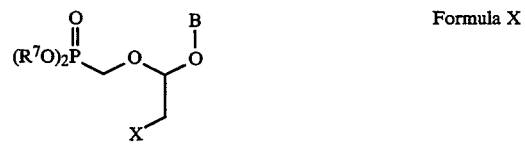

Formula X wherein
$R^7$ is $C_{1-4}$ alkyl, preferably $C_2$, or aryl;
X is I, or OAc; and
B is as defined in Formula VII.

As shown in Reaction Scheme 2, the compounds of Formula VII are prepared from the intermediates of Formulas VIII, IX and X as follows: paraformaldehyde is added to 2-(phenylselenyl)ethanol (26) in the presence of hydrochloric acid to give (2-phenylselenylethoxy)-methyl chloride (27). Displacement with triethyl phosphite gives the intermediate diethyl (2-phenylselenylethoxy)methylphosphonate (28). Oxidation of compound 28 followed by heating generates the novel intermediate diethylphosphonomethyl vinyl ether (18). Addition of $N_1$—O pyrimidine or $N_9$—O purine analogs to compound 18 in the presence of N-iodosuccinimide (NIS) gives the 6-N-(4',4''-dimethoxytrityl)-9-[3-iodo-2-(diethylphosphonomethoxy)ethoxy] purine or pyrimidine analog (19'). Displacement of iodide in the intermediate (19') with ammonium acetate gives the 6-N-(4',4''-dimethoxytrityl)-9-[3-acetoxy-2-(diethylphosphonomethoxy)ethoxy] purine or pyrimidine analog (20'). The 9-[2-hydroxy-2-(phosphonomethoxy)ethoxy] purine or pyrimidine analog (21') is then obtained by deblocking of the protecting groups.

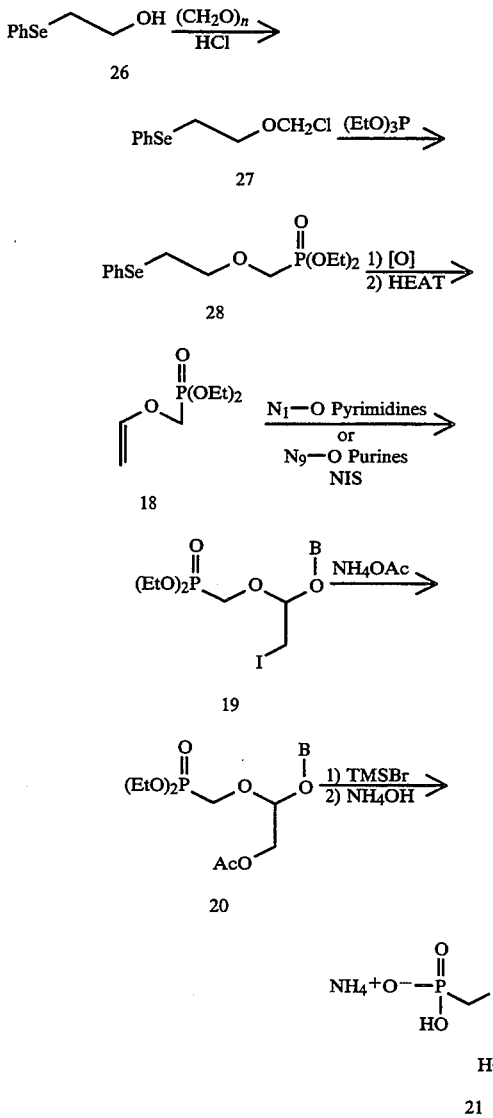

B = Pyrimidines
    Purines

Testing and Evaluation of Compounds against Herpesviruses and Retroviruses

Representative compounds of the present invention were evaluated for antiviral activity.

Herpes simplex virus (HSV) strains were grown and titered at 37° C. in vero cells (African Green Monkey Kidney cells) and used for virus work before the tenth passage.

Cells were grown and maintained in Earle's Minimum Essential Medium (EMEM), Gibco Laboratories, supplemented with 0.75% sodium bicarbonate, 2 mM 1-glutamine, Pen-strep. and 5-10% fetal calf serum.

The titer of HSV strains is determined by a plaque titration method (Roizman and Roane, Virology, 115: 75-79, 1961). Tissue culture 24-well petri dishes are seeded with cells and used for assays when approximately 75% monolayer. Volumes (0.1 ml) of logarithmic dilutions of the virus strain are inoculated onto each of triplicate wells, and absorbed for one hour with intermittent shaking. The inoculum thereafter is removed, and 1 ml of 5-10% EMEM containing 0.3% human immune serum globulin is added. After a 48 hour incubation period at 37° C. in a 5% $CO_2$ atmosphere, the overlay medium is removed and the cell sheets stained with Giemsa stain. The number of plaques is counted, the triplicate is averaged, and the number of plaque-forming units per ml is calculated.

The compounds are tested for activity against the herpes simplex stains using a stock solution of each compound freshly prepared. Appropriate dilution of each compound are made in 10% EMEM before usage. The antiviral efficacy of each compound is determined using the plaque reduction assay described above. Briefly, tissue culture 24-well plates, with approximately 50 plaque forming units of HSV per 0.1 ml, and the virus absorbed for 1 hour, with intermittent shaking. After removal of the inoculum, 1 ml of 10% EMEM containing two-fold dilutions of the appropriate drug are added in triplicates. Triplicate wells/plate receives no drug and are used as a virus control. After a 48-hour incubation period, at 37° C. in a 5% $CO_2$ atmosphere, the overlay medium is removed, the cells are stained as described above, and plaques are counted. The counts of triplicate wells are averaged, and the number of plaques in the presence of each drug dilution are calculated.

Human cytomegalovirus (HCMV) (strain AD169) was grown and titered at 37° C. in human embryonic lung (diploid) cells, MRC-5. The activity of compounds against HCMV was determined by using the procedure for the plaque reduction assay described above.

The compounds were evaluated for antiviral activity against murine leukemia virus (MuLV) strains using the UV-XC plaque assay (Rowe, et al., Virology, 42: 1136, 1970).

The MuLV strains were grown in feral mouse cells (SC-1) and used for antiviral tests using the UV-XC plaque assay. Briefly, SC-1 cells are grown as monolayers in 4-well tissue culture plates and inoculated with approximately 50-100 plaque forming units of MuLV in 0.5 ml of 5% EMEM containing 20 μg/ml DEAE/-Dextran. After 1 hour adsorption, the inoculum is removed and 5 ml of 5% EMEM containing three-fold dilutions of the appropriate drug are added. Five days later, the cultures are UV-irradiated with an ultraviolet lamp and rat XC sarcoma cells are added to the cultures. Three-four days after UV-irradiation, the cell cultures are stained with Giemsa stain and the plaques are enumerated. Antiviral activity is expressed in terms of the reduction in the mean number of UV-XC plaques counted in the drug treated, virus-infected cultures compared with mean number of plaques counted in untreated, virus-infected control cultures.

The antiviral potency of the drug is determined by $ID_{50}$, the drug concentration necessary to reduce the number of plaques by 50% of those in the virus control cultures.

Table 1 shows the antiviral test results of compound 14 against HSV-1, HSV-2 and HCMV. As shown in Table 1, compound 14 exhibited HSV-1 and HSV-2 activity comparable to acyclovir (ACV). Table 2 shows the antiviral test results of compound 21 against HSV-2, HCMV and MuLV. As shown in Table 2, compound 21 exhibited HSV-2 activity similar to ACV and HCMV activity comparable to DHPG. Compound 4 was tested for antiviral activity against HSV-2 and MuLV, and although compound 4 exhibited little activity against HSV-2 (ID$_{50}$: >100 μg/ml) it exhibited good activity against MuLV (ID$_{50}$: 1.5 μg/ml).

TABLE 1

Antiviral Test Results of Compound 14 against HSV-1 and HSV-2

| Compound | ID$_{50}$ (μg/ml) | | |
|---|---|---|---|
| | HSV-1 | HSV2 | HCMV |
| ACV | 0.6 | 0.7 | 40 |
| Compound 14 | 2.2 | 1.3 | 0.2 |

TABLE 2

Antivital Test Results of Compound 21 against HSV-2 and HCMV

| Compound | ID$_{50}$ (μg/ml) | | |
|---|---|---|---|
| | HSV-2 | HCMV | MULV |
| ACV | 0.35 | 40 | >100 |
| DHPG | 0.2 | 0.4 | >100 |
| Compound 21 | 2.6 | 1.0 | 1.5 |

The results of the above tests demonstrate that the compound of Formula VII exhibit antiviral and retroviral activity and therefore are useful in the treatment of viral and retroviral infections.

Accordingly, the present invention provides a method of treating viral and retroviral infections in a warm blooded animal in need thereof, which comprises administering to said animal an effective amount of at least one compound of Formula VII, alone or in admixture with a diluent or in the form of a medicament.

A further aspect of the present invention provides a pharmaceutical compositions comprising at least one compound of Formula VII in combination with a pharmaceutical carrier or diluent.

For therapeutic use, the pharmacologically active compounds of Formula VII will normally be administered as a pharmaceutical composition as the (or an) essential active ingredient at least one such compound in association with a pharmaceutically acceptable carrier and, optionally, with pharmaceutically acceptable adjuvants and excipients employing standard and conventional techniques. The reference *Remington's Pharmaceutical Sciences*, 17th Edition by A. R. Gennaro (Mack Publishing Company, 1985) discloses typical carriers and methods of preparation.

The pharmaceutical compositions may be administered topically or systemically to warm blooded animals, e.g., humans. By systemic administration is intended, oral, rectal, and parenteral (i.e., intramuscular, intravenous, subcutaneous and nasal) routes. Generally, it will be found that when a compound of the present invention is administered orally, a larger quantity of the reactive agent is required to produce the same effect as the smaller quantity given parenterally. In accordance with good clinical practice, it is preferred to administer the instant compounds at a concentration level that will produce effective antiviral effect without causing any harmful or untoward side effects.

Therapeutically and prophylactically the instant compounds are given as pharmaceutical compositions comprised of an effective antiviral or retroviral amount of a compound according to the invention or a pharmaceutically acceptable salt thereof and a pharmaceutically acceptable carrier, as stated hereinabove. Pharmaceutical compositions for effecting such treatment will contain a major or minor amount, e.g., from 95 to 0.5% of at least one compound of the present invention in combination with a pharmaceutical carrier, the carrier comprising one or more solid, semi-solid, or liquid diluents, fillers and formulation adjuvants which are non-toxic, inert and pharmaceutically acceptable. Such pharmaceutical compositions are preferable in dosage unit form; i.e., physically discrete units containing a predetermined amount of the drug corresponding to a fraction or multiple of the dose which is calculated to produce the desired therapeutic response. Other therapeutic agents can also be present. Pharmaceutical compositions providing from about 1 to 50 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents, (e.g., syrup, acacia, gelatin, sorbitol, tragacanth or polyvinylpyrrolidone), fillers (e.g., lactose, sugar, corn starch, calcium phosphate, sorbitol, or glycine), lubricants (e.g., magnesium stearate, talc, polyethylene glycol or silica), disintegrants (e.g., starch) and wetting agents (e.g., sodium lauryl sulfate). Solutions or suspensions of an inventive compound with conventional pharmaceutical vehicles are employed for parenteral compositions, such as an aqueous solution for intravenous injection or an oily suspension for intramuscular injection. Such compositions having the desired clarity, stability and adaptability for parenteral use are obtained by dissolving from 0.1% to 10% by weight of an active inventive compound in water or a vehicle comprising a polyhydric aliphatic alcohol such as glycerine, propylene glycol, and polyethylene glycol or mixtures thereof. The polyethylene glycols comprise a mixture of non-volatile, usually liquid, polyethylene glycols which are soluble in both water and organic liquids and have molecular weights from about 200 to 1500.

Considering the biological activities possessed by the compounds of the instant invention, it can be seen that these compounds have antiviral and retroviral properties, particularly suited to their use in combating viral and retroviral infections. Thus, another aspect of the instant invention concerns a process for treating viral (including retroviral) infections in a mammal in need of such treatment which comprises systemic or topical administration of such mammal of an effective dose of an inventive compound or a pharmaceutically acceptable salt thereof. On the basis of testing, an effective dose could be expected to be from about 0.1 to about 30 mg/kg body weight with about 1 to about 20 mg/kg body weight a preferred dosage range. It is envisioned that for clinical antiviral and retroviral application compounds of the instant invention will be administered in the same manner as for the reference drug acyclovir. For clinical applications, however, the dosage and dosage regimen must in each case be carefully adjusted, utilizing sound professional judgment and consideration of the age, weight and condition of the recipient, the route of administration and the nature and gravity of the illness. Generally, a daily dose will comprise from about 150 to about 750 mg, preferably 200 to 500 mg of an inventive compound administered from one to three times a day. In some instances, a sufficient therapeutic effect can be obtained at lower doses, while in others, larger doses will be required.

DESCRIPTION OF THE SPECIFIC EMBODIMENTS

The compounds which constitute the invention and their methods of preparation will appear more fully from a consideration of the following examples which are given for the purpose of illustration only and are not to be construed as limiting the invention in sphere or scope. The compounds which are not shown by specific example are readily prepared by analogous procedure.

It will be appreciated that the instant specification and claims are set forth by way of illustration and not limitation and that various modifications and changes may be made without departing from the spirit and scope of the present invention.

All compounds gave satisfactory elemental analyses.

In the following examples, all temperatures are understood to be in degrees C when not specified. The nuclear magnetic resonance (NMR), spectral characteristics refer to chemical shifts ($\delta$) expressed in parts per million (pp,) versus tetramethylsilane (TMS) as a reference standard. The relative area reported for the various shifts in the proton NMR spectral data corresponds to the number of hydrogen atoms of a particular functional type in the molecule. The nature of the shifts as to multiplicity is reported as broad singlets (bs), singlet (s), multiplet (m), doublet (d), doublet of doublets (dd), triplet (t) or quartet (q). Abbreviation employed are:

ACV—acyclovir
HIV—human immuno deficiency
HSV—herpes simplex virus
MuLV—murine leukemia virus
BID—twice a day
CDCl$_3$—deuterochloroform

EXAMPLE 1

Synthesis of 9-[[(Diethylphosphono)methoxy]methoxy]adenine (3)

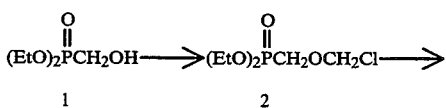

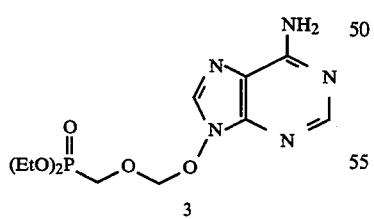

A solution of diethyl(hydroxymethyl)phosphonate (1) (8.0 g, 47.6 mmol) and 1,3,5-trioxane (1.56 g, 52 mmol) in 1,2-dichloroethane (35 mL) was saturated with HCl gas at 5° C. After stirring at 23° C. for 16 hours, the resulting solution was purged with a stream of N$_2$ to remove excess HCl and then dried with Na$_2$SO$_4$ and filtered. Concentration of the filtrate in vacuo gave compound 2 (80% purity as estimated by nmr) as a colorless oil: $^1$H NMR (CDCl$_3$) $\delta$ 1.42 (t, J=6.9 Hz, 6H), 3.92 (d, J=9.0 Hz, 2H). 4.05–4.20 (m, 4H), 5.45 (s, 2H). This material was used promptly for the next reaction without purification.

To a suspension of 60% sodium hydride in mineral oil (427 mg, 10.6 mmol) in dry DMF (75 mL) was added 9-hydroxy adenine (1.4 g, 9.7 mmol) [prepared according to the literature procedure: A. A. Watson *J. Org. Chem.*, 42, 1610 (1977)] and the mixture was heated at 80° C. for 1.5 hour under nitrogen. To this solution was added at 0° C. a solution of compound 2 (2.1 g, 9.7 mmol) in DMF (2 mL). The resulting mixture was stirred for 15 hours at 23° C. The mixture was then concentrated in vacuo, taken up in CH$_2$Cl$_2$ and washed with water and brine, dried over MgSO$_4$, and evaporated in vacuo. The residual oil was chromatographed on silica gel using CH$_2$Cl$_2$-5% MeOH as eluent to give compound 3 (886 mg, 35%) as a colorless oil: $^1$H NMR (CDCl$_3$) $\delta$ 1.29 (t, J=7.0 Hz, 6H), 4.02–4.13 (m, 4H), 4.15 (d, J=8.7 Hz, 2H), 5.31 (s, 2H), 6.10 (s, 2H), 8.06 (s, 1H), 8.30 (s, 1H).

EXAMPLE 2

Synthesis of 9-[(Phosphonomethoxy)methoxy]adenine ammonium salt (4)

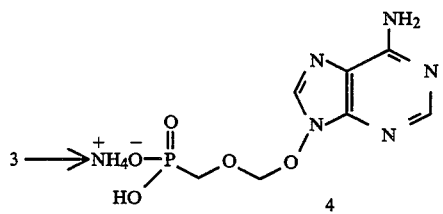

A solution of compound 3 (800 mg, 3.1 mmol) and bromotrimethylsilane (5 mL) in DMF (10 mL) was stirred at 5° C. for 90 minutes under nitrogen. The volatiles were removed in vacuo and the residual oil was dissolved in concentrated NH$_4$OH(10 mL). Water was evaporated in vacuo and the residual oil was purified by C$_{18}$ reverse phase column using water as eluent under 8 psi pressure to give 4 (264 mg, 29.5%) as a white solid: UV$_{max}$(H$_2$O) 260 nm ($\epsilon$ 11,674); $^1$H NMR (D$_2$O) $\delta$ 3.98 (d, J=9.0 Hz, 2H), 5.29 (s, 2H), 8.04 (s, 1H), 8.23 (s, 1H); $^{13}$C NMR (D$_2$O) $\delta$ 66.757, 68.832, 104.350, 104.507, 116,112, 140.825, 145,829, 154,194, 156,694.

Anal. Calcd for C$_7$H$_{13}$N$_6$O$_5$P.9H$_2$O: C, 27.27; H, 4.84; N, 27.25. Found: C, 27.02; H, 4.60; N, 26.95.

EXAMPLE 3

Synthesis of 4-N-Pivaloyl-1-benzyloxy cytosine (6)

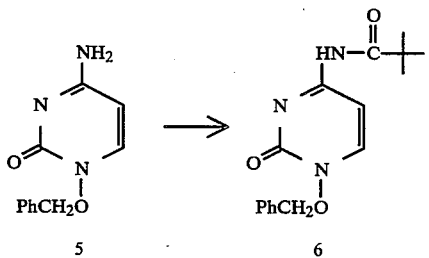

To a solution of compound 5 (3.4 g, 15.6 mmol) [prepared according to the literature procedure: W. Klotzer, *Monatsh. Chem.*, 96 169 (1965)] in pyridine (40 mL) and triethylamine (3.0 g, 30 mmol) was added pivaloyl chloride (2.4 g, 20 mmol). The solution was heated at 55° C. for 5 hours under nitrogen and then concentrated in vacuo. The residue was taken up in CH$_2$Cl$_2$ (120 mL), washed with 15% H$_3$PO$_4$ and water, dried over MgSO$_4$ and evaporated in vacuo. Column chromatography of the residual oil on silica gel using CH$_2$Cl$_2$-5% MeOH as eluent gave compound 6 (3,85 g, 83%) as an amorphous powder: $^1$H NMR (CDCl$_3$) δ 1.22 (s, 9H), 5.26 (s, 2H), 7.11 (d, J=7.8 Hz, 1H), 7.24 (d, J=7.8 Hz, 1H), 7.35 (s, 5H), 8.05 (broad s, 1H).

EXAMPLE 4

Synthesis of 4-N-Pivaloyl-1-hydroxycytosine (7)

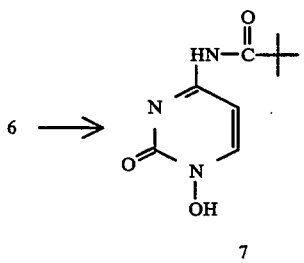

A mixture of compound 6 (3.0 g, 10 mmol) and 10% palladium on activated carbon (300 mg) in EtOH-EtOAc (1:1, 200 mL) was hydrogenated in the Parr hydrogenator at 20 psi for 15 minutes. The mixture was filtered through celite, washed with MeOH and the combined filtrate was evaporated in vacuo to give compound 7 (2.1 g, 100%) as a white solid: $^1$H NMR (DMSO-d$_6$) δ 1.02 (s, 6H), 7.18 (d, J=7.5 Hz, 1H), 8.25 (d, J=7.5 Hz, 1H), 10.23 (broad s, 1H).

EXAMPLE 5

Synthesis of 4-N-Pivaloyl-1-[[(diethylphosphono)methoxy]methoxy]cytosine (8)

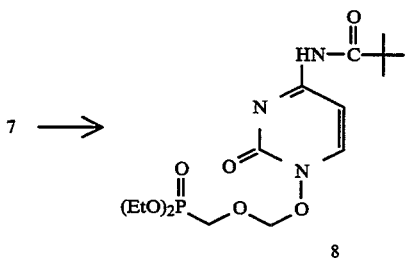

To a suspension of 60% sodium hydride in mineral oil (300 mg, 7.4 mmol) in dry DMF (75 mL) was added compound 7 (1.5 g, 17.4 mmol) and the mixture was stirred for 1 hour at 23° C. under nitrogen. To this solution was added at 0° C. a solution of compound 2 (2.1 g, 9.7 mmol) in DMF (2 mL). The resulting mixture was stirred for 15 hours at 23° C. The mixture was then concentrated in vacuo, taken up in CH$_2$Cl$_2$ and washed with water and brine, dried over MgSO$_4$, and evaporated. The residual oil was chromatographed on silica gel using CH$_2$Cl$_2$-5% MeOH as eluent to give 8 (1.75 g, 45%) as a white oil: $^1$H NMR (CDCl$_3$) δ 1.16 (s, 9H), 1.23 (t, J=8.5 Hz, 6H), 4.03 (d, J=9.3 Hz, 2H), 4.05 (q, J=8.5 Hz, 4H), 5.21 (s, 2H), 7.27 (d, J=7.5 Hz, 1H), 8.01 (d, J=7.5 Hz, 1H), 8.17 (broad s, 1H).

Anal. Calcd for C$_{15}$H$_{26}$N$_3$O$_7$P: C, 46.04; H, 6.65; N, 10.74. Found: C, 46.41; H, 6.46; N, 10.93.

EXAMPLE 6

Synthesis of 1-[[(Dimethylphosphono)methoxy]methoxy]cytosine (9)

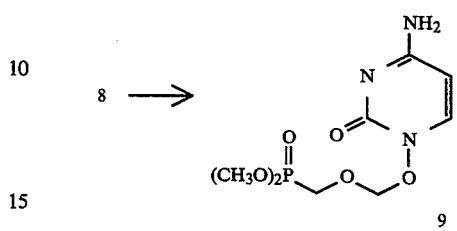

Sodium metal (368 mg, 16 mmol) was dissolved in anhydrous CH$_3$OH (25 mL) under nitrogen. To this solution was added compound 8 (1.55 g, 4.0 mmol) in MeOH (2 mL) and the solution was stirred for 15 hours at 23° C. The pH of the solution was adjusted to 8.0 by dropwise addition of concentrated HCl. All solvents were evaporated in vacuo and the residual oil was taken up in CH$_2$Cl$_2$, washed with water and brine, dried over MgSO$_4$, and evaporated. Column chromatography of the residual oil on silica gel using CH$_2$Cl$_2$-7% MeOH as eluent gave compound 9 (920 mg, 83%) as a white oil: $^1$H NMR (CDCl$_3$) δ 3.72 (d, J=10.2 Hz, 6H), 4.02 (d, J=9.3 Hz, 2H), 4.50 (broad s, 2H), 4.93 (s, 2H), 5.55 (d, J=7.5 Hz, 1H), 7.51 (d, J=7.5 Hz, 1H).

Anal Calcd for C$_8$H$_{14}$N$_3$O$_6$P: C, 34.41; H, 5.02; N, 15.05. Found: C, 34.43; H, 5.07; N, 15.35.

EXAMPLE 7

Synthesis of 1-[(Phosphonomethoxy)methoxy]cytosine ammonium salt (10)

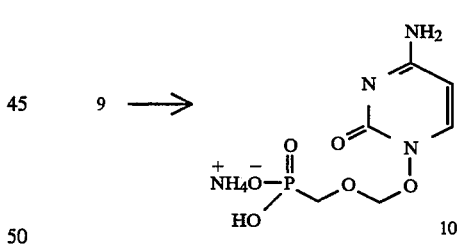

A solution of compound 9 (680 mg, 2.4 mmol) and bromotrimethylsilane (5 mL) in DMF (20 mL) was stirred at 23° C. for 7 hours under nitrogen. The volatiles were removed in vacuo and the residual oil was dissolved in concentrated NH$_4$OH (10 mL). Water was evaporated in vacuo and the residual oil was purified by C$_{18}$ reverse phase column using water as eluent to give compound 10 (225 mg, 35%) as white amorphous powder: UV$_{max}$ (H$_2$O) 274 nm (ε 7,329); $^1$H NMR (D$_2$O) δ 3.93 (d, J=9.3 Hz, 2H), 5.19 (s, 2H), 5.95 (d, J=7.5 Hz, 1H), 7.89 (d, J=7.5 Hz, 1H), $^{13}$C NMR (D$_2$O) δ 61.139 (d, J=157 Hz), 89.909, 96.560 (d, J=12 Hz), 141.423, 147.890, 158.930.

Anal. Calcd for C$_6$H$_{13}$N$_4$O$_6$P.1/2 H$_2$O: C, 25.09, H, 5.05; N, 20.21. Found: C, 25.29; H, 4.73, N, 19.99.

EXAMPLE 8

Synthesis of 2-Amino-6-methoxy-9-[[(dimethylphosphono)methoxy]methoxy]-purine (13)

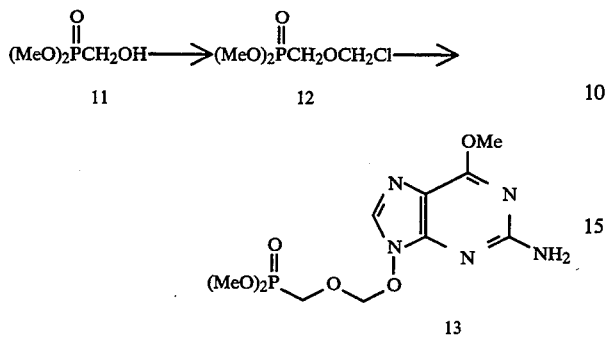

A solution of dimethyl(hydroxymethyl)phosphonate (11) (4 g, 28.6 mmol) and 1,3,5-trioxane (2.6 g, 28.6 mmol) in 1,2-dichloroethane (30 mL) was saturated with HCl gas at 5° C. After stirring at 23° C. for 18 hours, the resulting solution was purged with a stream of $N_2$ and then dried over $Na_2SO_4$ and filtered. Concentration of the filtrate gave compound 12 (85% purity as estimated by nmr) as a colorless oil: $^1$H NMR (CDCl$_3$) δ 3.78 (d, J=10.8 Hz, 6H), 3.90 (d, J=9.6 Hz, 2H), 5.48 (s, 2H). This material was used promptly for the next reaction without purification.

To a suspension of 60% sodium hydride in mineral oil (88 mg, 2.2 mmol) in dry (15 mL) was added 2-amino-6-methoxy-9-hydroxy-purine [prepared according to the patent procedure: M. R. Harnden, D. M. Duckworth, European Patent 0319228 (1989)] and the mixture was stirred at 23° C. for 1 hour under nitrogen. To this solution was added 0° C. a solution of compound 12 (400 mg, 2.1 mmol) in DMF (1 mL). The resulting solution was stirred for 16 h at 23° C. The mixture was then concentrated in vacuo. The residual oil was chromatographed on silica gel using CH$_2$Cl$_2$-10% MeOH as eluent to give compound 13 (338 mg, 48%) as a white oil: $^1$H NMR (CDCl$_3$) δ 3.73 (d, J=10.8 Hz, 6H), 3.97 (s, 3H), 4.19 (d, J=9.6 Hz, 2H), 5.21 (s, 2H), 5.25 (broad s, 2H), 7.73 (s, 1H); $^{13}$C NMR (CDCl$_3$) δ 53.518, 53.771, 61.804, 64.059, 102.099, 102.266, 112.265, 136.272, 149.964, 160.551, 162.467.

Anal. Calcd for C$_{10}$H$_{16}$N$_5$O$_6$P: C, 36.05; H, 4.85; N, 21.02. Found: C, 36.07; H, 4.62; N, 20.93.

EXAMPLE 9

Synthesis of 9-[(Phosphonomethoxy)methoxy]guanine ammonium salt (14)

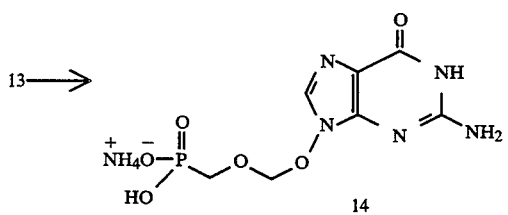

A solution of compound 13 (210 mg, 0.63 mmol) and bromotrimethylsilane (2 mL) in DMF (4 mL) was stirred at 10° C. for 2 hours under nitrogen. The volatiles were removed in vacuo and the residual oil was dissolved in concentrated NH$_4$OH (10 mL). Water was evaporated in vacuo and the residual solid was purified by C$_{18}$ reverse phase column using water as eluent under 8 psi pressue to give compound 14 (140 mg, 70%) as a white powder: UV$_{max}$ (H$_2$O) 252 nm (ε 12,192), 270 nm (ε 10,344); $^1$H NMR (D$_2$O) δ 3.94 (d, J=8.9 Hz, 2H) 5.27 (s, 2H), 7.95 (s, 1H); $^{13}$C NMR (D$_2$O) 6 67,686, 69.713, 104.411, 104,564, 113,933, 138,413, 148,829, 155.864, 160,314.

Anal. Calcd for C$_7$H$_{13}$N$_6$O$_6$P.1/2 H$_2$O: C, 26.50; H, 4.41; N, 26.50. Found: C, 26.86; H, 4.76; N, 26.19.

EXAMPLE 10

Synthesis of 6-N-[4',4"-(Dimethoxytrityl)]-9-benzyloxyadenine (16)

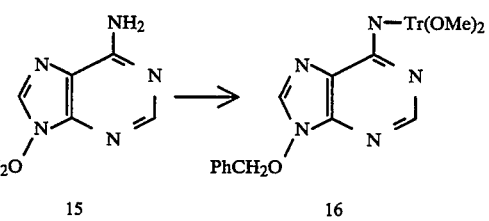

A solution of 9-benzyloxyadenine (6.0 g, 25 mmol) [prepared according to the published procedure: A. A. Watson, J. Org. Chem., 42 1610 (1977)] and 4,4'-dimethoxytrityl chloride (10.2 g, 30.8 mmol) in pyridine (40 mL) was heated at 75° C. for 4 hours under nitrogen. Pyridine was then evaporated in vacuo. The residual oil was taken up in CH$_2$Cl$_2$, washed with 20% H$_3$PO$_4$ and aqueous NaHCO$_3$, dried over MgSO$_4$ and filtered. Concentration of the filtrate gave a residual oil which was purified by column chromatography on silica gel using CH$_2$Cl$_2$-3% MeOH as eluent to give 16 (11.1 g, 86%) as a slightly yellow oil: $^1$H NMR (CDCl$_3$)3.72 (s, 6H), 5.28 (s, 2H), 6.80 (broad s, 1H), 6.7-7.3 (m, 19H), 8.05 (s, 1H).

EXAMPLE 11

Synthesis of 6-N-[4',4"-(Dimethoxytrityl)]-9-hydroxyadenine (17)

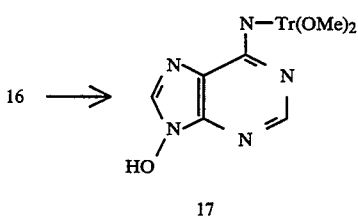

A mixture of compound 16 (1.8 g, 3.3 mmol) and 10% palladium on activated carbon (350 mg) in EtOH (120 mL) was hydrogenated in the Parr hydrogenator at 6 psi for 30 minutes. The mixture was filtered through celite, washed with EtOH and the filtrate was evaporated in vacuo to give 17 (1.2 g, 84%) as an amorphous powder: $^1$H NMR (CDCl$_3$) δ 3.73 (s, 6H), 6.7-7.2 (m, 13H), 7.85 (s, 1H), 7.89 (s, 1H).

EXAMPLE 12

Synthesis of Diethyl(2-phenylselenylethoxy)methylphosphonate (28)

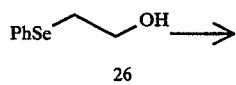

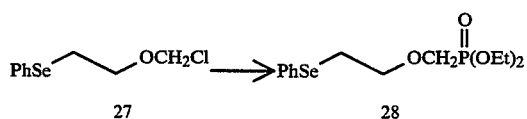

To a solution of 2-(phenylselenyl) ethanol (44 g, 0.22 mol) [prepared according to the literature procedure: P. Rollin, V. V. Bencomo, P. Sinay, Synthesis 13 (1984)] in $CH_2Cl_2$ (150 ml) was added paraformaldehyde (6.8 g, 0.23 mol). HCl gas was then bubbled into the solution at 5° C. for 2 hours. The reaction solution was dried ($MgSO_4$), and the solvent was removed in vacuo to give compound 27 as a colorless oil in quantitative yield. $^1$H-NMR (300 MHz, $CDCl_3$) of 27: δ 3.06 (t, J=7.0 Hz, 2H), 3.88 (t, J=7.0 Hz, 2H), 5.45 (s, 2H), 7.2–7.5 (m, 5H).

A solution of 27 (25 g, 0.1 mol) and triethyl phosphite was heated at 110° C. for 2.5 hours. After evaporation of volatile in vacuo, the residual oil was chromatographed on silica gel using $CH_2Cl_2$-6% MeOH as eluant to give 28 (30 g, 81%) as a slightly yellow oil. $^1$H-NMR (300 MHz, $CDCl_3$) δ 1.27 (t, J=7.24 Hz, 6H), 3.01 (t, J=7.5 Hz, 2H), 3.70–3.75 (m, 4H), 4.10–4.18 (m, 4H), 7.2–7.5 (m, 5H).

EXAMPLE 13

Synthesis of Diethylphosphonomethyl vinyl ether (18)

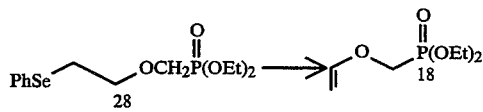

To a solution of 28 (30 g, 0.081 mol) in dioxane-methanol-water (6:2:1, 600 ml) was added sodium bicarbonate (34 g, 0.4 mol) followed by sodium periodate (51 g, 0.24 mol). After stirring for 30 minutes, the mixture was filtered. The filtrate was condensed to ca 100 ml volume diluted with $CH_2Cl_2$ (500 ml) and washed with brine. Evaporation of dried ($MgSO_4$) solvent gave a colorless oil which was dissolved in benzene (200 ml). Diisopropylamine (30 g, 0.3 mol) was added and the solution was heated at 90° C. for 30 minutes. All volatiles were removed in vacuo and the residual oil was chromatographed on silica gel using $CH_2Cl_2$—MeOH (3%) as eluent to give 18 (15.3 g, 95%) as a colorless oil. $^1$H-NMR (300 MHz, $CDCl_3$) δ 1.25 (T, J=7.2 Hz, 6H), 3.86 (d, J=9.6 Hz, 2H), 4.01–4.15 (m, 5H), 4.20 (dd, J=3.6, 14.7 Hz, 1H), 6.42 (dd, J=6.6, 14.7 Hz, 1H).

EXAMPLE 14

Synthesis of 6-N-(4′,4″-Dimethoxytrityl)-9-[3-iodo-2-(diethylphosphonomethoxy)ethoxy]adenine (19)

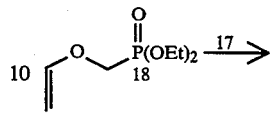

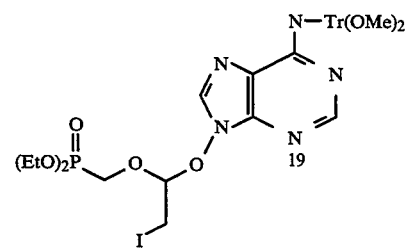

To a solution of compound 17 (2.1 g, 4.5 mmol) and compound 18 (1.2 g, 6 mmol) in $CH_2Cl_2$ at 0° C. was added N-iodosuccinimide (1.4 g, 6 mmol) portionwise over 3 minutes under nitrogen. The mixture was stirred for 2 hours at 0° C., and then diluted with $CH_2Cl_2$. The $CH_2Cl_2$ was washed with 10% sodium bisulfite, brine and dried over $MgSO_4$. The filtrate was concentrated in vacuo and the residual oil was chromatographed on silica gel using $CH_2Cl_2$-3% MeOH as eluent to give compound 19 (1.9 g, 55%) as a slightly yellow oil: $^1$H NMR ($CDCl_3$) δ 1.32 (t, J=6.5 Hz, 6H), 3.25 (dd, J=7.2, 12.0 Hz, 1H), 3.55 (dd, J=3.3, 12.0 Hz, 1H), 3.74 (s, 6H), 4.1–4.3 (m, 6H), 5.39 (dd, J=3.3, 7.2 Hz, 1H), 6.70 (d, J=8.7 Hz, 4H), 7.1–7.3 (m, 10H), 8.02 (s, 1H).

EXAMPLE 15

Synthesis of 9-N-(4′,4″-Dimethyoxytrityl)-9-[3-acetoxy-2-(diethylphosphono-methoxy)ethoxy]adenine (20)

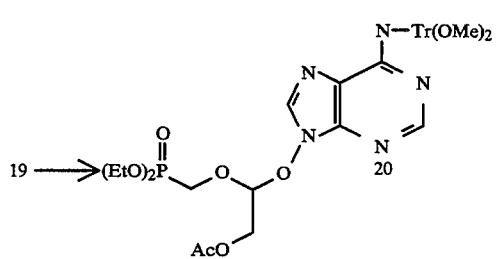

A solution of compound 19 (1.7 g, 2.2 mmol) and tetraethylammonium acetate tetrahydrate (1.8 g, 6.7 mmol) in DMF (20 mL) was heated at 55° C. for 4 hours under nitrogen. Volatiles were removed in vacuo, and the residual oil was taken up in $CH_2Cl_2$, washed with water, brine and dried over $MgSO_4$. The filtrate was concentrated in vacuo and the residual oil was chromatographed on silica gel using $CH_2Cl_2$-3% MeOH as eluent to give 20 (740 mg, 48%) as a white oil: $^1$H NMR ($CDCl_3$) δ 1.31 (t, J=6.5 Hz, 6H), 2.11 (s, 3H), 3.77 (s, 6H), 4.3–4.5 (M, 8H), 5.53 (t, J=6.0 Hz, 1H), 6.76 (d, J=11.1 Hz, 4H), 8.02 (s, 1H), 8.83 (s, 1H).

EXAMPLE 16

Synthesis of
9-[2-Hydroxy-2-(phosphonomethoxy)ethoxy]adenine ammonium salt (21)

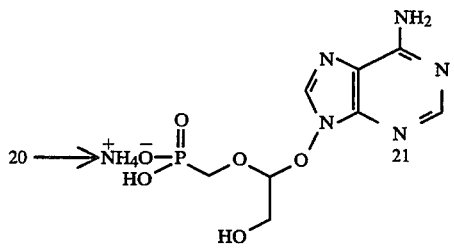

A solution of compound 20 (705 mg, 1.0 mmol) and bromotrimethylsilane (2 mL) in DMF (3 mL) was stirred at 5° C. for 1 hour under nitrogen. The solution was continuously stirred for 2 hours without cooling bath. The volatiles were removed in vacuo and the residue was dissolved in concentrated NH$_4$OH (5 mL). After stirring at 23° C. for 2 hours, water was evaporated in vacuo and the residual solid was purified by C$_{18}$ reverse phase column using water as eluent to give compound 21 (129 mg, 40%) as a white amorphous powder: UV$_{max}$ (H$_2$O) 260 nm (ε 8,372); $^1$H NMR (D$_2$O) δ 3.71 (d, J=4.5 Hz, 2H), 3.81 (dd, J=9.3, 11.2 Hz, 1H), 3.99 (dd, J=9.3, 11.2 Hz, 1H), 4.82 (m, 1H), 5.37 (t, J=4.8 Hz, 1H), 8.14 (s, 1H), 8.27 (s, 1H); $^{13}$C NMR (D$_2$O) δ 61.752, 66,849, 68,928, 111,909, 112.065, 116,348, 141,614, 147,052, 153.506, 156.438.

Anal. Calcd for C$_8$H$_{15}$N$_6$O$_6$P.3/4 H$_2$O: C, 28.61; H, 4.91; N, 25.00. Found: C, 28.05; H, 5.24; N, 25.04.

EXAMPLE 17

Synthesis of
4-N-pivaloyl-1-[3-Iodo-2-(diethylphosphonomethoxy)ethoxy]cytosine (22)

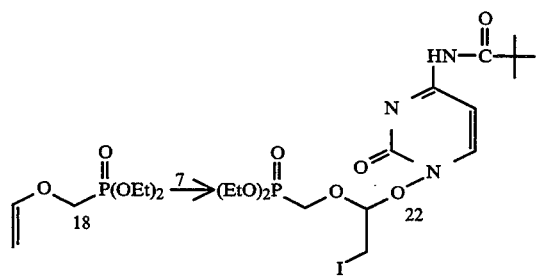

To a suspension of compound 7 (2.78 g, 13.2 mmol) and compound 18 (2.81 g, 14.5 mmol) in CH$_2$Cl$_2$ (50 mL) was added at 0° C. portionwise N-iodosuccinimide (3.0 g, 13.7 mmol) over 10 minutes. The mixture was stirred at 0° C. for 60 minutes, and then diluted with CH$_2$Cl$_2$ (50 mL). The CH$_2$Cl$_2$ was washed with 10% sodium bisulfite, and dried over MgSO$_4$. The filtrate was concentrated in vacuo and the residual oil was chromatographed on silica gel using CH$_2$Cl$_2$-3% MeOH qs eluent to give compound 22 (2.6 g, 37%) as a white powder: $^1$H NMR (CDCl$_3$) δ 1.23 (s, 9H), 1.29 (t, J=6.9 Hz, 6H), 3.32 (dd, J=6.3, 8.7 Hz, 1H), 3.50 (dd, J=3.6, 8.7 Hz, 1H), 4.40–4.2 (m, 6H), 4.69 (broad s, 1H), 5.35 (dd, J=2.8, 3.0 Hz, 1H), 7.34 (d, J=7.8 Hz, 1H), 7.92 (d, J=7.8 Hz, 1H).

Anal. Calcd for C$_{16}$H$_{27}$N$_3$O$_7$IP: C, 36.16, H, 5.08; N, 7.91. Found: C, 36.38; H, 5.02; N, 8.27.

EXAMPLE 18

Synthesis of
4-N-Pivaloyl-1-[3-acetoxy-2-(diethylphosphonomethoxy)ethoxy]cytosine (23)

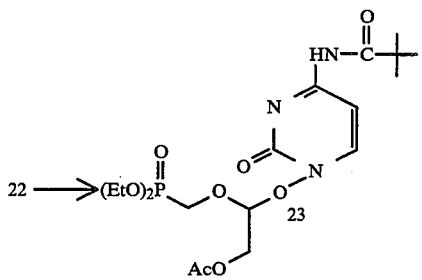

A mixture of compound 22 (1.78 g, 3.4 mmol) and cesium acetate (3.2 g, 16.8 mmol) in DMF (6 mL) was heated at 80° C. for 90 minutes under nitrogen. The volatiles were removed in vacuo and the residual mixture was taken up in CH$_2$Cl$_2$. The CH$_2$Cl$_2$ was then washed with water, brine and dried over MgSO$_4$. The filtrate was evaporated in vacuo and the residual oil was chromatographed on silica gel using CH$_2$Cl$_2$-5% MeOH as eluent to give compound 23 (530 mg, 35%) as a white oil: $^1$H NMR (CDCl$_3$) δ 1.25 (s, 9H), 1.30 (t, J=7.0 Hz, 6H), 2.05 (s, 3H), 4.0–4.15 (m, 4H), 4.25 (dd, J=4.5, 8.8 Hz, 1H),4.33 (dd, J=4.5, 8.8 Hz, 1H), 5.54 (t, J=4.8 , 1H), 7.33 (d, J=7.8 Hz, 1H), 7.90 ( d, J=7.8 Hz, 1H).

EXAMPLE 19

Synthesis of
1-[3-Hydroxy-2-(dimethylphosphono)ethoxy]cytosine (24)

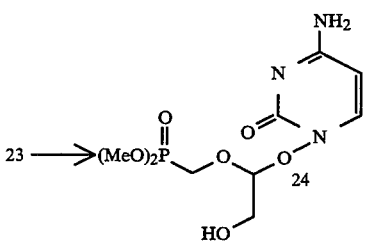

A solution of compound 23 (450 mg, 0.99 mmol) and sodium methoxide (185 mg, 18 mmol) in methanol (10 mL) was stirred at 23° C. for 18 hours under nitrogen. The reaction was carefully neutralized to pH 5.0 by dropwise addition of 20% H$_3$PO$_4$ in an ice bath, and diluted with CH$_2$Cl$_2$—MeOH (1:1, 50 mL). The mixture was filtered and the filtrate was evaporated in vacuo. The residual oil was chromatographed on silica gel using CH$_2$Cl$_2$-10% MeOH as eluent to give 24 (198 mg, 65%) as a white oil: $^1$H NMR (CD$_3$OD) δ 3.60 (d, J=5.7 Hz, 6H), 3.62–3.66 (m, 2H), 3.82 (dd, J=9.0, 10.9 Hz, 1H), 3.97 (dd, J=9.0, 10.9 Hz, 1H), 5.20 (t, J=4.8 Hz, 1H), 5.83 (d, J=7.5 Hz, 1H), 7.86 (d, J=7.5 Hz, 1H); $^{13}$C NMR (CD$_3$OD) δ 52.935 (d,J=5.3 Hz), 61,744, 66,264 (d, J=160 Hz), 96.198, 111.288, 147.410, 156.903, 167.359.

EXAMPLE 20

Synthesis of
1-[3-Hydroxy-2-(phosphonomethoxy)ethoxy]cytosine
(25)

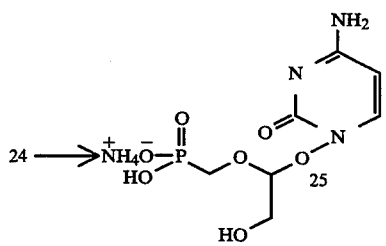

A solution of compound 24 (300 mg, 1.0 mmol) and trimethyl-silylbromide (0.7 mL) in DMF (4 mL) was stirred at 23° C. for 2 hours under nitrogen. Volatiles were removed in vacuo and the residue was dissolved in concentrated NH$_4$OH (2 mL). Water was evaporated in vacuo, and the residual solid was purified by C$_{18}$ reverse phase column using water as eluent under 8 psi pressure to give compound 25 (133 mg, 46%) as a white powder: UV max (H$_2$O) 275 nm ($\epsilon$ 7,650); $^1$H NMR (D$_2$O) $\delta$ 3.67–3.75 (m, 3H), 3.84 (dd, J=8.9, 10.8 Hz, 1H), 5.19 (t, J=4.4 Hz, 1H), 5.88 (d, J=7.7 Hz, 1H), 7.77 (d, J=7.7 Hz, 1H); $^{13}$C NMR (D$_2$O) $\delta$ 62,097, 69,420 (d, J=151 Hz), 97,729, 111.256 (d, J=11.1 Hz), 147,318, 157,023, 166.890.

What is claimed is:

1. An intermediate having the formula

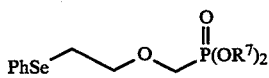

wherein R$^7$ is alkyl C$_{1-4}$ or aryl.

2. An intermediate having the formula

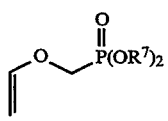

wherein R$^7$ is alkyl C$_{1-4}$ or aryl.

3. A process for preparing the compound having the formula

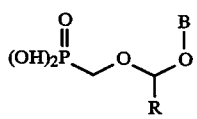

wherein
R is hydrogen, alkyl having 1 to 6 carbon atoms, hydroxyalkyl with 1 to 6 carbon atoms, or haloalkyl having 1 to 6 carbon atoms;
B is a purine base selected from the group consisting of guanine, 8-bromoguanine, 8-chloroguanine, 8-aminoguanine, 8-hydrazinguanine, 8-hydroxyguanine, 8-methylguanine, 8-thioguanine, 3-deazaguanine, adenine, 3 deazaadenine, 2-aminopurine, 2,6-diaminopurine, xanthine or hypoxanthine, or B is a pyrimidine base selected from the group consisting of cytosine, 5-ethylcytosine, 5 methylcytosine, thymine, pyrimidine, uracil, 5-chlorouracil, 5-bromouracil, 5-ethyluracil, 5-iodouracil, 5-propyluracil or 5-vinyluracil, which process comprises adding paraformaldehyde to diethyl(hydroxymethyl)phosphonate in the presence of hydrochloric acid to give diethyl(chloromethoxy)methylphosphonate, followed by displacement with N$_1$—O pyrimidines or N$_9$—O purine analogs to give the 9-[[diethylphosphono)-methoxy]methoxy] purine or 1-[[diethylphosphono)methoxyl]-methoxy pyrimidine analogs, then deblocking of the protecting group to give 9-[(phosphonomethoxy)methoxy]purine or pyrimidine ammonium salt.

4. A process for preparing a compound having the formula

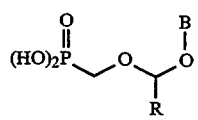

which process comprises stirring a solution of a compound having the formula

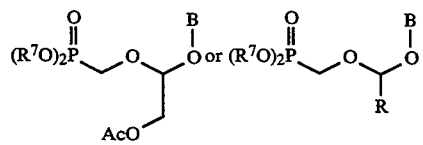

and bromotrimethyl silane in DMF at 5° C. for about one hour under nitrogen whereby R$^7$ is removed, then removing the volatiles and dissolving the residue in a concentrated NH$_4$OH solution followed by evaporating the solution to obtain the compound, wherein
B is a purine or pyrimidine base;
R is hydrogen, alkyl C$_{1-6}$, hydroxyalkyl C$_{1-6}$ or haloalkyl C$_{1-6}$; and
R$^7$ is alkyl C$_{1-4}$ or aryl.

5. A process for preparing the compound of the formula

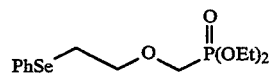

which process comprises adding paraformaldehyde to (phenylselenyl)ethanol in the presence of hydrochloric acid to give (2-phenylselenylethoxy)methyl chloride followed by displacement with triethyl phosphite.

6. A process for preparing a compound of the formula

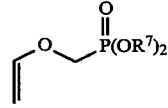

wherein R$^7$ is alkyl C$_{1-4}$, or aryl which process comprises oxidation of a compound of the formula

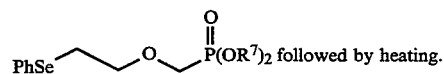

7. A process for preparing a compound of the formula

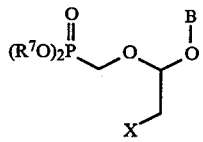

or isomers or solvates thereof wherein $R^7$ is alkyl $C_{1-4}$, or aryl; X is I; and B is a purine or pyrimidine base which process comprises addition of an $N_1$—O pyrimidine or an $N_9$—O purine analog to a compound of the formula

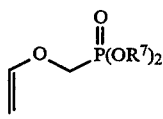

in the presence of N-iodosuccinimide.

8. A process for preparing a compound of formula

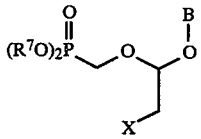

or isomers or solvates thereof wherein $R^7$ is alkyl $C_{1-4}$ or aryl; X is OAc and B is a purine or pyrimidine base which process comprises displacement with ammonium acetate of iodide in the compound of formula

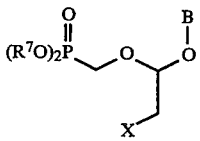

wherein X is I and B is a purine or pyrimidine base.

9. An intermediate of the formula

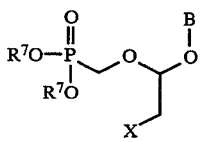

or isomers or solvates thereof wherein
X is I or OAc;
B is $N^4$-pivaloylpyrimidine or $N^4$-(4',4''-dimethoxytrityl)pyrimidine, $N^6$-(4',4''-dimethoxytrityl)purine; and
$R^7$ is H, $C_{1-4}$ alkyl or aryl or a pharmaceutically acceptable salt thereof.

10. An intermediate of the formula

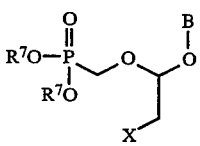

wherein B is $N^4$-pivaloylcytosine, $N^4$-pivaloyl-5-methylcytosine, $N^4$-pivaloyl-5-ethylcytosine, $N^4$-(4',4''-dimethoxytrityl)cytosine, $N^4$-(4',4''-dimethoxytrityl)-5-methylcytosine, $N^4$-(4',4''-dimethoxytrityl)-5-ethylcytosine, $N^6$-(4',4''-dimethoxytrityl)adenine, $N^6$-(4',4''-dimethoxytrityl)-2,6-diaminopurine or $N^6$-(4',4''-dimethoxytrityl)-3-deazaadenine;
X is I Or OAc; and
$R^7$ is H, $C_{1-4}$ alkyl or aryl.

11. The intermediate of claim 7 wherein B is thymine, uracil, 5-ethyluracil, 5-chlorouracil, 5-bromouracil, 5-iodouracil, 5-propyluracil, 5-vinyluracil, $N^4$-pivaloylcytosine, $N^4$-pivaloyl-5-methylcytosine, $N^4$-pivaloyl-5-ethylcytosine, $N^4$-(4',4''-dimethoxytrityl)cytosine, $N^4$-(4',4''-dimethoxytrityl)-5-methylcytosine, $N^4$-(4',4''-dimethoxytrityl)-5-ethylcytosine, $N^6$-(4',4''-dimethoxytrityl)adenine, $N^6$-(4',4''-dimethoxytrityl)-2,6-diaminopurine, 2-amino-6-methoxypurine or $N^6$-(4',4''-dimethoxytrityl)-3-deazaadenine.

12. The intermediate of claim 8 wherein B is thymine, uracil, 5-ethyluracil, 5-chlorouracil, 5-bromouracil, 5-iodouracil, 5-propyluracil, 5-vinyluracil, $N^4$-pivaloylcytosine, $N^4$-pivaloyl-5-methylcytosine, $N^4$-pivaloyl-5-ethylcytosine, $N^4$-(4',4''-dimethoxytrityl)cytosine, $N^4$-(4',4''-dimethoxytrityl)-5-methylcytosine, $N^4$-(4',4''-dimethoxytrityl)-5-ethylcytosine, $N^6$-(4',4''-dimethoxytrityl)adenine, $N^6$-(4',4''-dimethoxytrityl)-2,6-diaminopurine, 2-amino-6-methoxypurine or $N^6$-(4',4''--dimethoxytrityl)-3-deazaadenine.

13. The process of claim 4 further comprising the step of purifying the compound by reverse phase column chromatography.

* * * * *